(12) United States Patent
Mou et al.

(10) Patent No.: US 8,597,667 B2
(45) Date of Patent: Dec. 3, 2013

(54) TARGETED AND INDIVIDUALIZED COSMETIC DELIVERY

(75) Inventors: Tsung-Wei Robert Mou, Stony Brook, NY (US); Fatemeh Mohammadi, Hauppauge, NY (US); Lisa Qu, Flushing, NY (US); Tamar Lara Kamen, New York, NY (US); Anna Czarnota, Huntington Station, NY (US)

(73) Assignee: ELC Management LLC, New York, NY (US)

( * ) Notice: Subject to any disclaimer, the term of this patent is extended or adjusted under 35 U.S.C. 154(b) by 477 days.

(21) Appl. No.: 12/410,118

(22) Filed: Mar. 24, 2009

(65) Prior Publication Data

US 2009/0280150 A1 Nov. 12, 2009

Related U.S. Application Data

(63) Continuation of application No. 12/410,118, filed on Mar. 24, 2009.

(60) Provisional application No. 61/051,774, filed on May 9, 2008, provisional application No. 61/097,273, filed on Sep. 16, 2008.

(51) Int. Cl.
*A61L 15/16* (2006.01)
(52) U.S. Cl.
USPC .............................. 424/401; 424/444; 424/449
(58) Field of Classification Search
None
See application file for complete search history.

(56) References Cited

U.S. PATENT DOCUMENTS

| 3,154,070 A | 10/1964 | Meckelburg |
| 3,499,446 A | 3/1970 | Tsuneizumi et al. |
| 5,016,173 A | 5/1991 | Kenet et al. |

(Continued)

FOREIGN PATENT DOCUMENTS

| DE | 102005020938 A1 | 11/2006 |
| EP | 1030267 | 8/2000 |

(Continued)

OTHER PUBLICATIONS

PCT International Search Report; International Application No. PCT/US2009/041618; Completion Date: Dec. 4, 2009; Date of Mailing: Dec. 4, 2009.

(Continued)

*Primary Examiner* — Anand Desai
*Assistant Examiner* — Melissa Mercier
(74) *Attorney, Agent, or Firm* — Cynthia R. Miller

(57) ABSTRACT

A system and methods are provided for targeted and individualized delivery of multiple skin benefit agents to the skin of a user. The image of a predetermined treatment area of the user's skin is first captured by an imaging device. The captured image data is then analyzed by a computing device to generate a unique skin profile for the user. Based on such skin profile, a printing device prints out one or more cosmetic delivery sheets that can be applied to the predetermined treatment area. Each of the cosmetic delivery sheets contains a substrate with multiple isolated, discrete regions, while at least two of the regions are imprinted with different skin benefit agents for treating different skin conditions of the predetermined treatment area according to the unique skin profile of the user. Targeted delivery of one or multiple skin benefit agents to the skin of a user may be achieved by applying and conforming to the skin a flexible cosmetic delivery sheet having associated therewith the multiple skin benefit agents.

4 Claims, 6 Drawing Sheets

(56) References Cited

U.S. PATENT DOCUMENTS

| | | | |
|---|---|---|---|
| 5,538,732 A * | 7/1996 | Smith et al. | 424/402 |
| 5,622,692 A | 4/1997 | Rigg et al. | |
| 5,958,560 A | 9/1999 | Ewan | |
| 6,001,380 A | 12/1999 | Smith et al. | |
| 6,293,284 B1 | 9/2001 | Rigg | |
| 6,502,583 B1 | 1/2003 | Utsugi | |
| 6,516,245 B1 | 2/2003 | Dirksing et al. | |
| 6,530,379 B2 | 3/2003 | Iosilevich | |
| 6,571,003 B1 | 5/2003 | Hillebrand et al. | |
| 6,574,801 B1 | 6/2003 | Harens et al. | |
| RE38,246 E | 9/2003 | Leonard et al. | |
| 6,761,697 B2 | 7/2004 | Rubinstenn et al. | |
| 6,770,286 B1 | 8/2004 | Berry | |
| 6,810,130 B1 | 10/2004 | Aubert et al. | |
| 6,856,861 B2 | 2/2005 | Dirksing et al. | |
| 6,937,755 B2 | 8/2005 | Orpaz et al. | |
| 6,959,119 B2 | 10/2005 | Hawkins et al. | |
| 7,006,657 B2 | 2/2006 | Bazin | |
| 7,079,158 B2 | 7/2006 | Lambertsen | |
| 7,165,559 B1 | 1/2007 | Goodman | |
| 7,324,668 B2 | 1/2008 | Rubinstenn et al. | |
| 7,387,787 B2 * | 6/2008 | Fox | 424/443 |
| 7,424,139 B1 | 9/2008 | Stefan et al. | |
| 7,437,344 B2 | 10/2008 | Peyrelevade | |
| 7,634,103 B2 | 12/2009 | Rubinstenn et al. | |
| 8,077,931 B1 | 12/2011 | Chatman et al. | |
| 2002/0090123 A1 | 7/2002 | Bazin | |
| 2003/0063794 A1 | 4/2003 | Rubinstenn et al. | |
| 2004/0022830 A1 | 2/2004 | Nakamura et al. | |
| 2004/0078278 A1 | 4/2004 | Dauga et al. | |
| 2004/0102750 A1 | 5/2004 | Jameson | |
| 2006/0104931 A1 | 5/2006 | Fukutome et al. | |
| 2006/0197775 A1 | 9/2006 | Neal | |
| 2007/0258656 A1 | 11/2007 | Aarabi | |
| 2008/0014231 A1 | 1/2008 | Okano | |
| 2008/0058915 A1 | 3/2008 | Chang | |
| 2008/0163344 A1 | 7/2008 | Yang | |
| 2009/0129631 A1 | 5/2009 | Faure et al. | |
| 2009/0133206 A1 * | 5/2009 | Benjamin et al. | 15/227 |
| 2009/0231356 A1 | 9/2009 | Barnes et al. | |
| 2009/0260648 A1 | 10/2009 | Castelluccio | |
| 2010/0226531 A1 | 9/2010 | Goto | |

FOREIGN PATENT DOCUMENTS

| | | | |
|---|---|---|---|
| EP | 1433418 A1 | 6/2004 | |
| EP | 1 459 782 | 9/2004 | |
| EP | 1813167 | 8/2007 | |
| JP | 55-164623 A | 12/1980 | |
| JP | 55160717 | 12/1980 | |
| JP | 7-231883 | 9/1995 | |
| JP | 08-308634 | 11/1996 | |
| JP | H10-255066 | 9/1998 | |
| JP | H11-169231 | 6/1999 | |
| JP | 2001-346627 | 12/2001 | |
| JP | 2004-501707 | 1/2004 | |
| JP | 2006-519263 | 8/2006 | |
| KR | 20-0416534 | 5/2006 | |
| KR | 10-2008-0059157 | 6/2008 | |
| TW | 200426655 | 12/2004 | |
| WO | WO97/29441 | 8/1997 | |
| WO | WO98/37811 | 9/1998 | |
| WO | WO00/00059 | 1/2000 | |
| WO | WO01/04840 | 1/2001 | |
| WO | WO 02/01499 | 1/2002 | |
| WO | WO2004/078122 | 9/2004 | |
| WO | WO2005/058114 | 6/2005 | |
| WO | WO2007/006559 | 1/2007 | |
| WO | WO2007/021972 | 2/2007 | |
| WO | WO2007/123380 | 11/2007 | |
| WO | WO 2008/010167 | 1/2008 | |
| WO | WO2009/137277 | 11/2009 | |

OTHER PUBLICATIONS

PCT Written Opinion of the International Searching Authority, or the Declaration; International Application No. PCT/US2009/041618; Completion Date: Dec. 4, 2009; Mailing Date: Dec. 4, 2009.

PCT International Search Report; International Application No. PCT/US2009/052525; Completion Date: Feb. 25, 2010; Date of Mailing: Mar. 2, 2010. (Related U.S. Appl. No. 12/533,107).

PCT Written Opinion of the International Searching Authority, or the Declaration; International Application No. PCT/US2009/052525; Completion Date: Feb. 25, 2010; Mailing Date: Mar. 2, 2010. (Related U.S. Appl. No. 12/533,107).

Supplementary European Search Report; EP09814947; Completion Date: Oct. 10, 2011; Date of Mailing: Oct. 24, 2011.

PCT International Search Report; International Application No. PCT/US2011/036288; Completion Date: Jan. 31, 2012; Date of Mailing: Feb. 9, 2012.

PCT Written Opinion of the International Searching Authority; International Application No. PCT/US2011/036288; Completion Date: Jan. 31, 2012; Mailing Date: Feb. 9, 2012.

PCT International Search Report; International Application No. PCT/US2011/036292; Completion Date: Jan. 31, 2012; Date of Mailing: Feb. 9, 2012.

PCT Written Opinion of the International Searching Authority; International Application No. PCT/US2011/036292; Completion Date: Jan. 31, 2012; Mailing Date: Feb. 9, 2012.

* cited by examiner

TARGETED AND INDIVIDUALIZED COSMETIC DELIVERY

The present application is a continuation of U.S. Ser. No. 12/410,118, filed Mar. 24, 2009, which claims priority from U.S. 61/051,774, filed May 9, 2008, and 61/097,273, filed Sep. 16, 2008.

FIELD OF THE INVENTION

The present invention relates to a method for the targeted and individualized delivery of one or more skin benefit agents to the skin of an user in need of such skin benefit agents, and to devices in the form of a single-use sheet for containing and delivering the skin benefit agents to one or more targeted areas of the skin. In particular, the invention relates to a method of delivering one or more skin benefit agents to targeted areas of the facial skin of a user based on the unique skin profile of such user and to a cosmetic sheet mask which incorporates one or more cosmetic or dermatological preparations for application to and treatment of the targeted areas of the skin of the user.

BACKGROUND OF THE INVENTION

A variety of cosmetic patches or devices are commercially marketed or described as being useful for the delivery of skin care actives such as vitamins, anti-acne actives, moisturizers, and the like. It has been known to use cosmetic sheets comprised of various materials, such as non-woven cotton, elastically extendable or stretchable materials, thermoplastics, tacky gel, etc., impregnated with various cosmetic or dermatological preparations, for application to the skin of the face, the neck and other areas of the body. The cosmetic sheets comprise a flexible support adapted to conform to the target areas when applied. The sheets also contain a system for containing and delivering skin benefit agents to the skin to which the sheet is applied. Currently, however, facial sheet masks on the market are fully impregnated with active ingredients and are applied to the entire face so as to deliver these ingredients to the entire face. Alternatively, a patch is applied only to certain areas, such as, under the eyes, to deliver the skin benefit agent to only this locus. However, these articles suffer drawbacks resulting in undesirable in-use characteristics as perceived by the consumer. For example it has heretofore not been possible with known full facial masks to target one or more specific areas with one or more skin benefit agents, but only to treat the entire face with one composition. Most consumers have different concerns for their skin in different areas of their face. For example many consumers have combination skin in which the T-zone area (forehead, nose and chin) is oily while the remainder of the face is dry. For another example some consumers may have lines and wrinkles at the forehead, eye, and mouth areas, dry or flaky skin at the cheek areas, and hyperpigmentation spots at other areas. Each region would need different treatment products to address the different concerns. Conventional masks can only address one concern at a time by treating the entire facial skin, rather than only the targeted areas.

There is therefore a need by consumers for cosmetic sheets which can deliver multiple skin benefit agents to various targeted areas of the skin of a user to address different skin conditions of such a user based on his or her unique skin profile.

SUMMARY OF THE INVENTION

The cosmetic sheets according to the present invention are provided with discrete regions, which are imprinted with different skin benefit agents, so when such cosmetic sheets are applied to and conformed to the skin, they can accurately deliver predetermined dosages of different skin care formulations to the skin for treating different skin conditions or providing different skin benefits. More preferably, the cosmetic sheets of the present invention are not mass-produced like the conventional "one-type-fits-all" products, but are specifically customized for individual users according to their unique skin profiles.

Accordingly, the present invention in one aspect relates to a system for targeted and individualized delivery of multiple skin benefit agents to the skin of a user. Such system includes at least: (a) an imaging device for capturing an image of a predetermined treatment area of the user's skin; (b) an analyzing device communicatively connected with the imaging device for receiving data representative of the captured image from the imaging device, analyzing such data, and generating a skin profile indicative of the conditions of the predetermined treatment area of the user's skin; and (c) a printing device communicatively connected with the analyzing device for printing one or more cosmetic delivery sheets, wherein the cosmetic delivery sheets are arranged and constructed for conforming to the predetermined treatment area of the user's skin, wherein each of the cosmetic delivery sheets comprises a substrate with multiple isolated, discrete regions, wherein at least two of the isolated, discrete regions are imprinted with different skin benefit agents for treating different skin conditions of the predetermined treatment area according to the skin profile generated by the analyzing device.

The present invention in another aspect relates to a cosmetic delivery sheet arranged and constructed for conforming to a predetermined treatment area of the skin of a user. Such a cosmetic delivery sheet includes at least a substrate with multiple isolated, discrete regions, wherein at least two of the isolated, discrete regions are imprinted with different skin benefit agents for treating different skin conditions of the predetermined treatment area.

The present invention in a further aspect relates to a printer that contains cartridges filled with compositions containing skin benefit agents. Such a printer is constructed to print the skin benefit agents onto a substrate through a heatless printing process.

The present invention in yet another aspect relates to a method for targeted and individualized delivery of multiple skin benefit agents to the skin of a user, which includes at least: (a) capturing an image of a predetermined treatment area of the user's skin; (b) analyzing the captured image data; (c) generating a skin profile indicative of the conditions of the predetermined treatment area of the user's skin; and (d) printing one or more cosmetic delivery sheets based on the generated skin profile, wherein the cosmetic delivery sheets are arranged and constructed for conforming to the predetermined treatment area of the user's skin, wherein each of the cosmetic delivery sheets comprises a substrate with multiple isolated, discrete regions, wherein at least two of the isolated, discrete regions are imprinted with different skin benefit agents for treating different skin conditions of the predetermined treatment area.

The present invention in yet a further aspect relates to a method for the targeted delivery of a skin benefit agent to the skin, which includes, in one embodiment, applying to the skin in need of a skin benefit agent a cosmetic delivery sheet being shaped and sufficiently flexible to conform to the skin of a user when adhered thereto. The cosmetic delivery sheet comprises a support having first and second opposite surfaces. The cosmetic sheet may be comprised of one or more layers. Each opposite surface may be comprised of one or a plurality of layers. The first surface is adapted to be applied to the skin in need of the benefit agent, and has associated therewith at least one cosmetic composition comprising an effective amount of at least one skin benefit agent for releasable delivery to a targeted area of the skin in need of the benefit agent. The cosmetic composition is associated with the first surface in at least one isolated, discrete region having well-defined edges, the isolated, discrete region having an area which is less than the entire area of the cosmetic sheet, for releasable delivery to a targeted area of the skin in need of the benefit agent. The second surface of the support is imprinted in at least one predetermined area corresponding to the at least one isolated, discrete region associated with the first surface of the support. Once conformed to the skin, the user manipulates the sheet with the fingertips in the one or more imprinted predetermined areas in a manner indicated by the imprinting so as to release the at least one cosmetic composition to a targeted area of the skin underlying the isolated, discrete region and deliver an effective amount of the at least one skin benefit agent to the targeted area of the skin underlying the at least one isolated, discrete region. In a second embodiment, the cosmetic delivery sheet includes a support having first and second opposite surfaces and an interior region disposed between said first and second surfaces, and at least one cosmetic composition, comprising at least one skin benefit agent, which is contained in and carried by the support. Each opposite surface may be comprised of one or a plurality of layers. The interior region has at least one isolated, discrete region having well-defined edges, the isolated, discrete region having an area which is less than the entire area of the cosmetic sheet, for retaining the at least one cosmetic composition therein and for the releasable delivery of the at least one skin benefit agent to a targeted area of the skin in need of the benefit agent. The first surface of the support is adapted to be applied to the skin in need of the benefit agent, and the second surface is imprinted in at least one predetermined area corresponding to the at least one isolated, discrete region. Each imprinted predetermined area overlies a corresponding isolated, discrete region. Each isolated, discrete region is impregnated with the at least one cosmetic composition including at least one skin benefit agent, and the skin benefit agent may be the same or different in each of the regions. Once conformed to the skin, the user manipulates the sheet with the fingertips in the one or more imprinted predetermined areas in a manner indicated by the imprinting so as to express the at least one cosmetic composition from the interior region and through the first surface of the cosmetic sheet to a targeted area of the skin underlying the isolated, discrete region and deliver an effective amount of the at least one skin benefit agent to the targeted area of the skin underlying the at least one isolated, discrete region.

As used herein, the term "imprinted" is intended to refer to any symbol or a combination of symbols provided on the second surface of the cosmetic sheet for the purpose of distinguishing or designating an area or areas on the second surface which corresponds to a discrete area on the first surface of or in the interior region of the cosmetic sheet which is associated with a skin benefit agent. Non-limiting examples of imprinting may encompass, for example, a stamp, an impression, an etching, an inscription, a graphic, a mark, a label, or a patch, which would satisfy the intended purpose. An "effective amount" means an amount of the skin benefit agent sufficient to be delivered to a targeted skin area to achieve the desired treatment results.

Other aspects and objectives of the present invention will become more apparent from the ensuing description, examples, and claims. Further aspects may include, for example, a kit comprising the targeted cosmetic delivery sheet and instructions for applying and using the sheet to deliver the skin benefit agent to the skin in need of such treatment. The instructions may be provided, for example, in written form or in the form of software.

Figure 1:
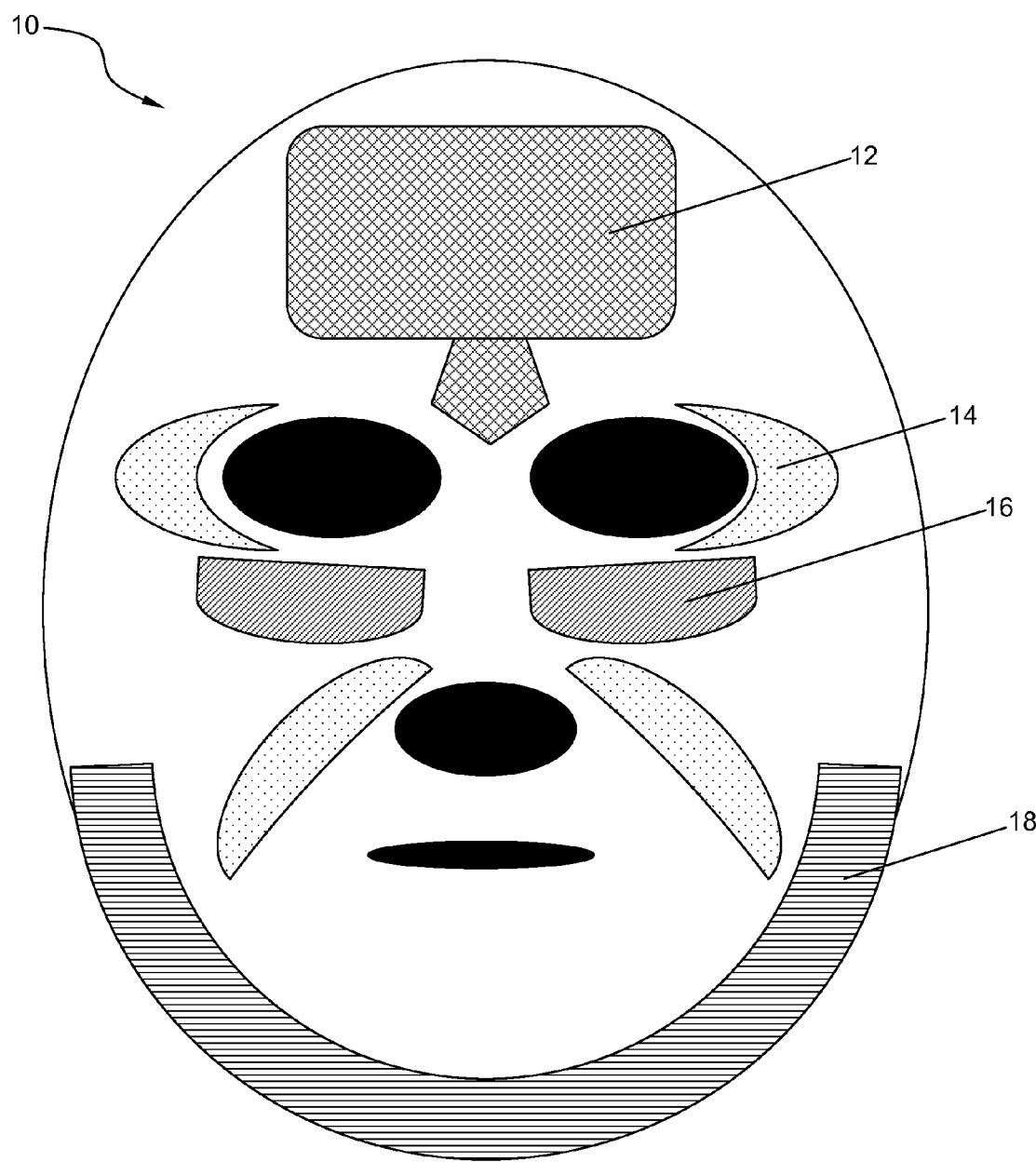
FIG. 1 is a schematic representation of a facial mask containing multiple isolated, discrete regions with different skin benefit agents, according to one embodiment of the present invention.

DETAILED DESCRIPTION OF THE INVENTION
AND PREFERRED EMBODIMENTS THEREOF

Reference will now be made in detail to exemplary embodiments of the invention. It is contemplated that a computerized or computer-aided system is used for achieving the targeted and individualized delivery of multiple skin benefit agents to the skin of a user based on the unique skin profile of the user. Cosmetic delivery products produced by the system of the present invention are capable of delivering multiple skin benefit agents to multiple target sections or regions on demand and according to the user skin profile with precise dosage and location control.

Preferably, such a system includes at least an imaging device for capturing an image of the desired treatment area of the user's skin. Such desired treatment skin area may be, for example, full face, partial face, neck, thigh, or the like. In a particularly preferred but not necessary embodiment of the present invention, the desired treatment area is the full face of the user. The imaging device is preferably a digital camera, which may capture the images of the desired treatment area in conjunction with a light source that delivers sufficient and consistent visible or invisible light, such as infrared light or near infrared light. The imaging device can be set in either a manual or an automatic mode for identifying the desired treatment area.

The captured images are directly converted by such imaging device into digital data and stored therein or sent to a personal computer or other computerized analyzing device that is communicatively connected with the imaging device. The analyzing device is programmed for analyzing image data and generating a skin profile indicative of the conditions of the desired treatment area of the user's skin based on the image data. Preferably, the skin profile defines skin regions with certain defects that need certain types of treatment. The term "defects" as used herein broadly covers any types of sub-optimal skin conditions, such as skin dryness, flakiness, redness, oiliness, large pores, dullness, dark spots, uneven skin tone, acne scars, fine lines and wrinkles, under-eye dark circles, under-eye puffiness, cellulite, and the like, or any types of abnormal skin conditions or disorders. More preferably, the skin profile also defines the severity of the skin defects. Such skin profile can be generated using various known algorithms. Examples of these algorithms are described in greater detail by Japanese Patent Application Publication No. 95-231883 entitled "Skin Surface Analysis System and Skin Surface Analysis Method"; International Patent Application Publication No. WO98/37811 entitled "Systems and Methods for the Multispectral Imaging and Characterization of Skin Tissue"; and U.S. Pat. No. 5,016,173 entitled "Apparatus and Method for Monitoring Visually Accessible Surfaces of the Body," the contents of which are incorporated in their entireties for all purposes. If the severity of the skin defects is represented by a numerical value, it may be desirable to normalize such value based on the user's ethnic origin, age, geographic location, or any other factor that may have an impact on the user's skin conditions.

Once the skin profile is generated, it is outputted by the analyzing device to a printing device, which correspondingly prints out one or more cosmetic delivery sheets that are customized for the user based on his or her unique skin conditions. Preferably, the printing device is a printer that contains multiple cartridges, each of which is filled with a composition containing one or more skin benefit agents. Because the conventional vaporization-based printing mechanism requires heating of the ink tank, which may degrade or destabilize certain skin benefit agents, it is preferred that the printing in the present invention is carried out using a heatless printing mechanism. For example, a pressure-driven ink jet can be used, in which pressure is created on demand by a piezoelectric transducer to change the shape of an internal diaphragm in the ink tank and therefore force droplets of the skin benefit agents contained in the ink tank to be deposited onto the substrate.

By using the above-described heatless printing process, the present invention can successfully achieve delivery of multiple skin benefit agents with little or no reduction in their biological activities. First, the heatless printing process causes little or no degradation of the skin benefit agents. Second, certain skin benefit agents that are known to interfere with each other's biological activities can be placed into separate cartridges and deposited onto the substrate as separate droplets. More importantly, the droplets of such interfering skin benefit agents are sufficiently small in size that they can be arranged in a scattered manner. Consequently, such skin benefit agents can provide simultaneous treatments to the same region, but without having to be mixed with each other.

The cosmetic delivery sheets so printed could be used anywhere on the face or body skin to predetermined areas for delivery of ingredients via a sheet material mask or patch or similar system. The exact size and shape of the cosmetic sheet will depend upon the intended use and product characteristics. The cosmetic sheets will have sufficient flexibility, and a size and shape adapted to conform to the desired treatment area of the user's skin. In a particularly preferred, but not necessary, embodiment of the present invention, the cosmetic sheet is a facial mask adapted to conform to facial features. It will be understood that a variety of shapes and sizes may be accommodated according to the invention. Such a cosmetic sheet mask may include a flexible substrate that is formed of preferably but not necessarily water-soluble materials, such as water-soluble film-forming polymers. The substrate contains multiple isolated, discrete regions, while at least two of such regions are imprinted with different skin benefit agents for treating different skin conditions according to the skin profile of the user.

Suitable skin benefit agents can be used in the present invention include, but are not limited to: anti-wrinkle or skin-tightening agents; anti-aging agents; moisturizing agents; skin-whitening or depigmentation agents; anti-inflammatory agents; skin soothing agents; anti-acne agents; DNA repair agents; skin lipid barrier repair agents; anti-cellulite agents; wound-healing agents; stretch-mark/scar removing agents; plumping agents; hair growth retardation agents; hair growth stimulating agents; dark cycle reduction or de-puffing agents; collagen synthesis or blood circulation enhancing agents; antioxidants; sebum-controlling agents; and pore-minimizing agents. Exemplary anti-wrinkle agents include, but are not limited to, retinoids, hydroxyacids, peptides, such as acetyl hexapeptide-8, palmitoyl oligopeptide, dipeptide diaminobutyroyl, benzylamide diacetate, and the like. Exemplary skin-tightening agents include, but are not limited to, algae extract, pullulan, sweet almond seed extract, carbomer, palmitoyl oligopeptide, palmitoyl tetrapeptide-7, *Quercus suber* extract, polymers such as proteins, polysaccharides, acrylic or methacrylic acid-containing polymers, and the like. Exemplary anti-aging agents include, but are not limited to, teprenone, trisodium resveratrol triphosphate, *Polygonum cuspidatum* root extract, whey protein, and the like. Exemplary moisturizing agents include, but are not limited to, hyaluronic acid, glycerin, urea, trehalose, coconut oil, muru muru butter, propylene glycol, glyceryl triacetate, polyols such as sorbitol, xylitol, maltitol, polydextrose, lactic acid, and the like. Exemplary skin-whitening or depigmentation agents include, but are not limited to, ascorbic acid, magnesium ascorbyl phosphate, aminopropyl ascorbyl phosphate, mulberry root extract, *Scutellaria baicalensis* extract, grape extract, ferulic acid, hinokitol, kojic acid, arbutin, licorice extract, and the like. Exemplary anti-inflammatory agents include, but are not limited to, spike moss extract, seal whip extract, *Polygonum cuspidatum* root extract, amatoflavone, grapeseed extract, colloidal gold, and the like. Exemplary skin soothing agents, include, but are not limited to, aloe, meadowfoam seed oil, caffeine, and the like. Exemplary anti-acne agents include, but are not limited to, salicylic acid, glycolic acid, lactobionic acid, sulfur, resorcinol, benzoyl peroxide, and the like. Exemplary DNA repair agents include, but are not limited to, C1-C8 alkyl tetrahydroxycyclohexanoate, micrococcus lysate, bifida ferment lysate, and the like. Exemplary skin lipid barrier repair agents include, but are not limited to, phytosphingosine, linoleic acid, cholesterol, and the like. Exemplary anti-cellulite agents include, but are not limited to, *Coleus forskohlii* root extract, *Magnolia grandiflora* bark extract, *Nelubo nucifera* leaf extract, and the like. Exemplary wound-healing agents include, but are not limited to, *Mimosa tenuiflora* bark extract, soybean protein, and the like. Exemplary plumping agents include, but are not limited to, *Saccharomyces*/xylinum black tea ferment, *Anemarrhena asphodeloides* root extract, sodium hyaluronate, and the like. Exemplary hair growth retardation agents include, but are not limited to, ursolic acid, phytosphingosine, *Boswella serrata* extract, and the like. Exemplary hair growth stimulating agents include, but are not limited to, *Serenoa serrulata* fruit extract, licorice extract, acetyl glucosamine, and the like. Exemplary dark circle reduction or de-puffying agents include, but are not limited to, hesperidin methyl chalcone, dipeptide-2, *Passiflora incarnate* flower extract, linoleic acid, isolinoleic acid, and the like. Exemplary collagen synthesis or blood circulation enhancing agents include, but are not limited to, arginine, *Ascophyllum nodosum* extract, *Asparagopsis armata* extract, caffeine, and the like. Exemplary anti-oxidants include, but are not limited to, nordihydroguaiaretic acid, grape seed extract, green tea leaf extract, and the like.

Figure 2:
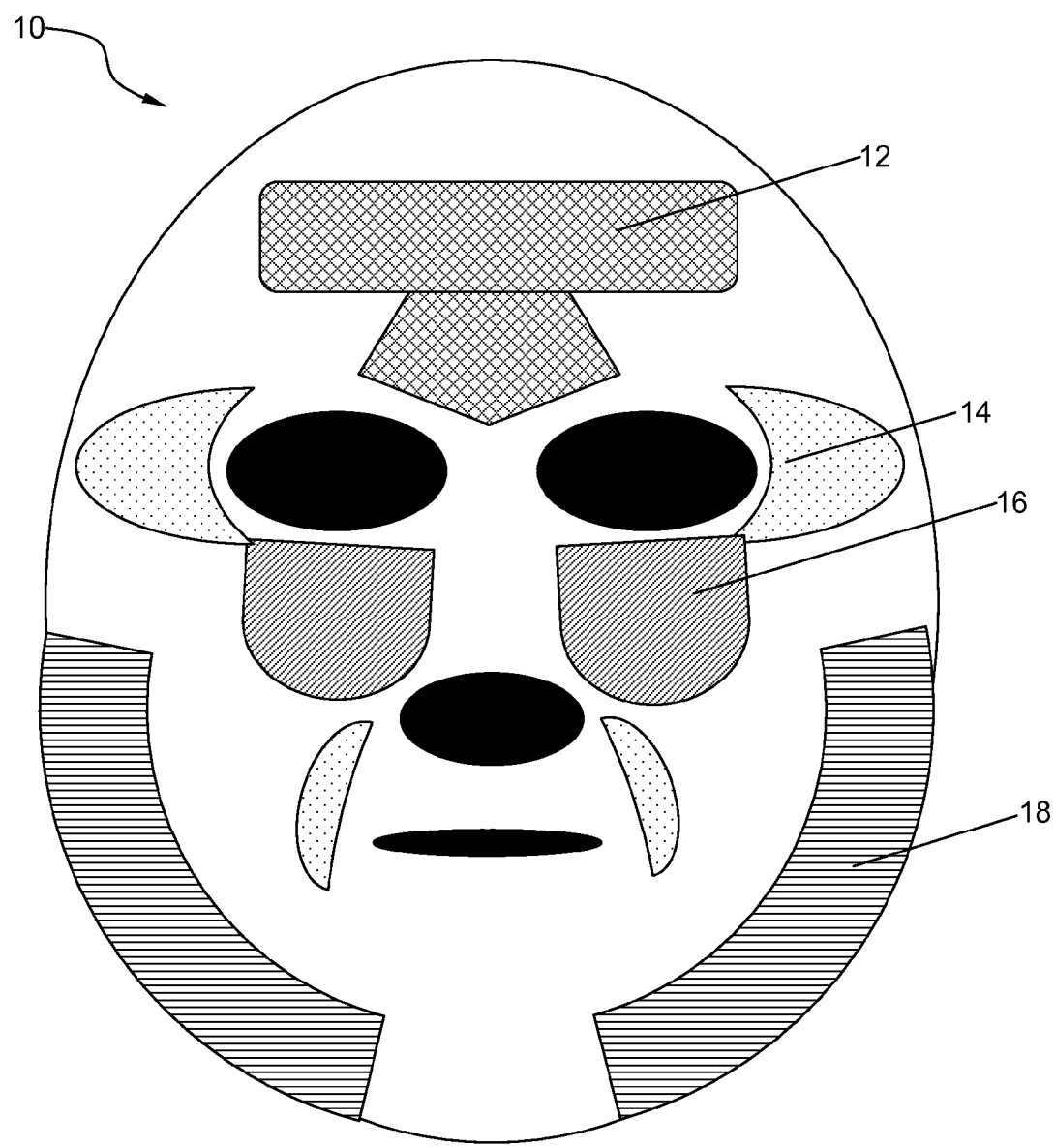
FIG. 2 is a schematic representation of a facial mask according to a second embodiment of the present invention.

FIG. 1 is a schematic view of a facial mask 10 according to one embodiment of the present invention. The facial mask 10 contains multiple discrete regions 12, 14, 16, and 18, which are isolated from one another. Based on the particular skin conditions of the user, regions 12 are imprinted with at least one sebum controlling agent for reducing the oiliness at the T-zone section of the user's face; regions 14 are imprinted with at least one wrinkle reduction or skin-tightening agent for reducing the fine lines and wrinkles at the corners of the user's eyes and mouth; regions 16 are imprinted with at least one dark circle reduction or de-puffying agent; and region 18 is imprinted with at least one anti-cellulite agent. Of course, the discrete regions themselves, may also be customized based on a skin profiling analysis. Customizations include size, shape and number of discrete regions. FIG. 2 is a schematic representation of a facial mask 10 according to a second embodiment of the present invention.

Figure 3:
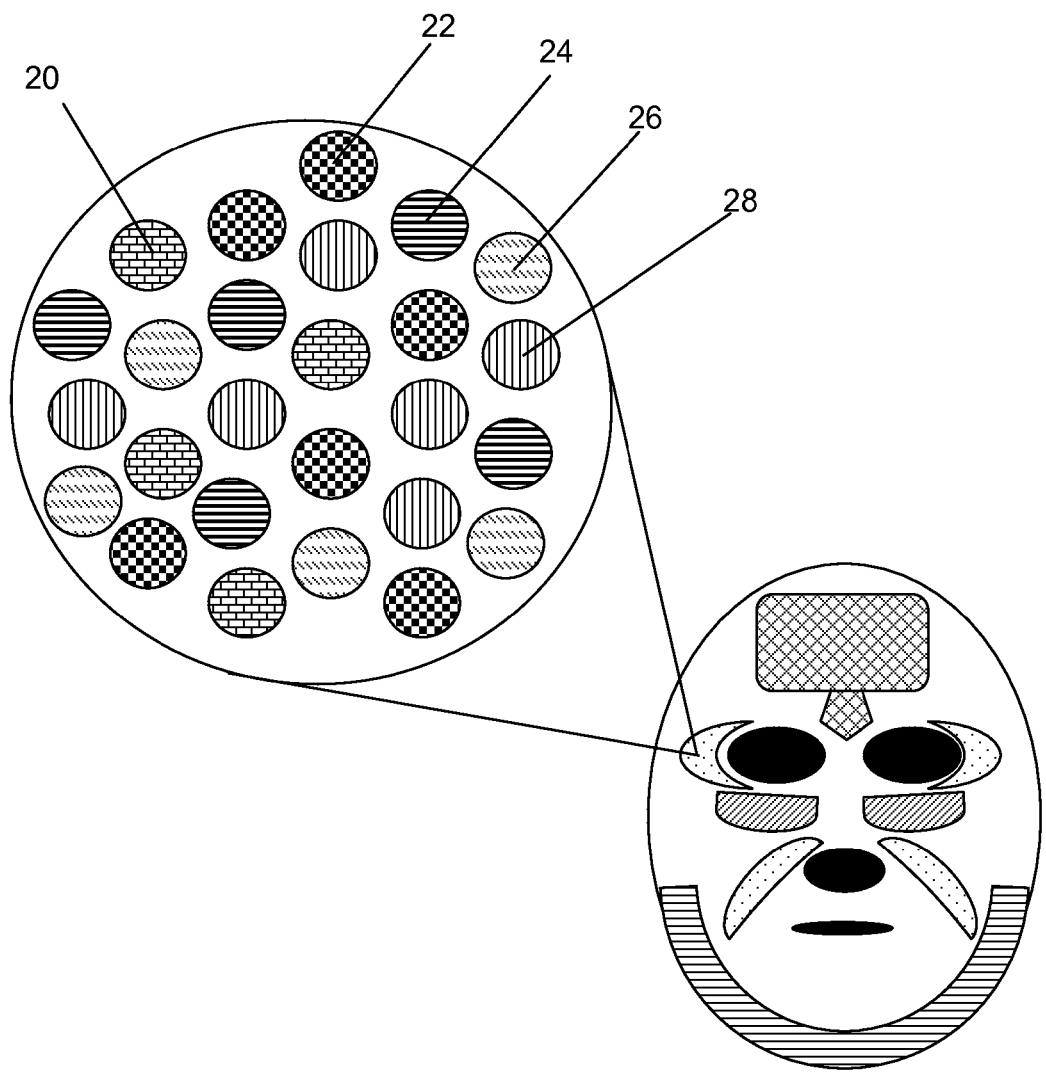
FIG. 3 is an exploded view of one isolated, discrete region on the facial mask of FIG. 1.

FIG. 3 shows an exploded view of the region 14 of FIG. 1. Five different types of skin benefit agents are printed thereon, which include a wrinkle reduction or skin-tightening agent 20, an anti-aging agent 22, an antioxidant agent 24, a moisturizing agent 26, and a plumping agent 28. These skin benefit agents are deposited onto the substrate as separate droplets, which are scattered among one another but without being mixed with one another. In this manner, such skin benefit agents can provide simultaneous treatment to the corners of the user's eyes and mouth with minimum or no interference with one another.

Figure 4:
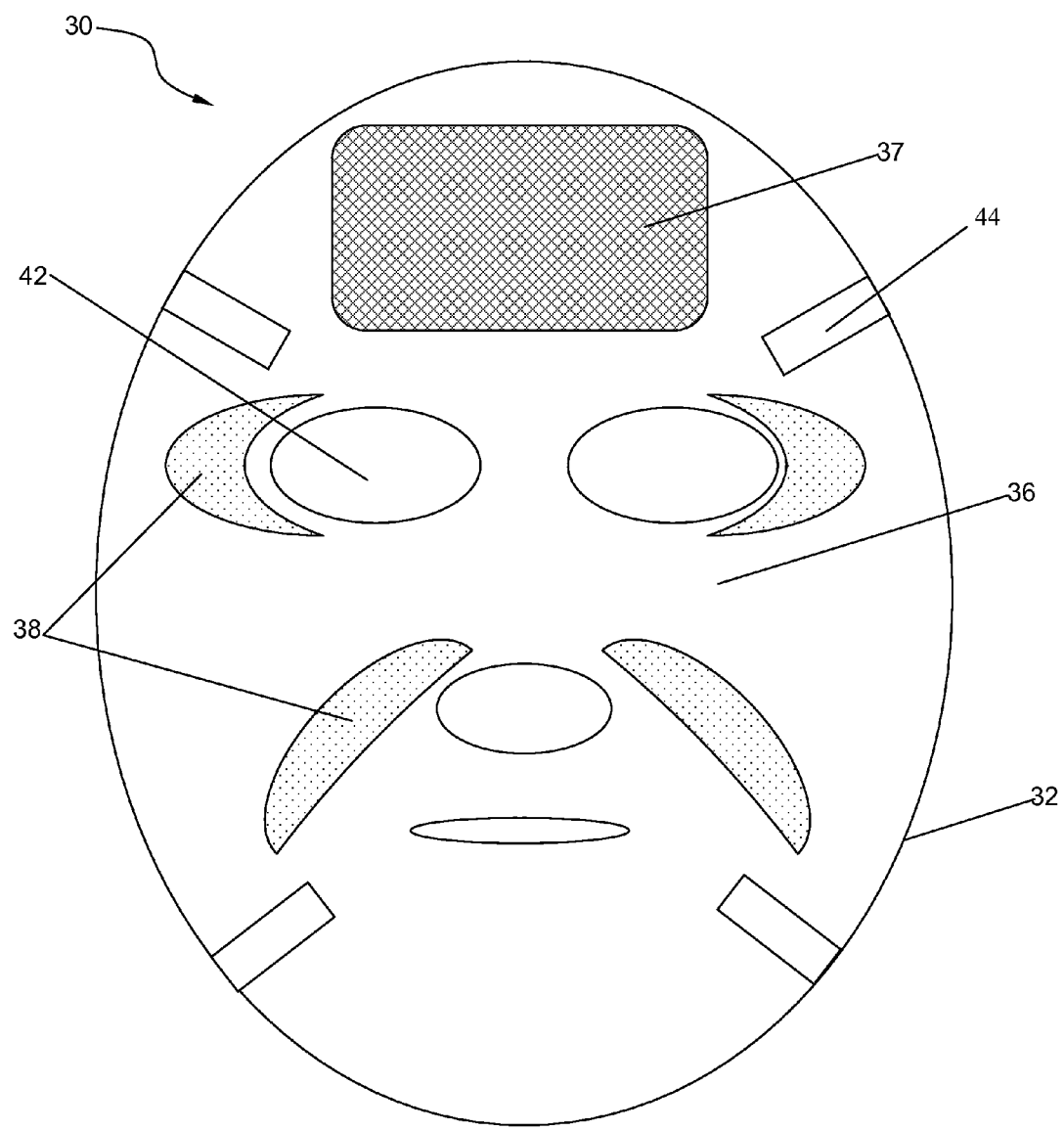
FIG. 4 is a schematic representation of a facial mask according to a third embodiment of the present invention.

FIG. 4 illustrates a cosmetic sheet designated generally by the numeral 30. The cosmetic sheet mask 30 has a configuration adapted to conform to facial features. It will be understood that a variety of shapes and sizes may be accommodated according to the invention. The cosmetic sheet mask 30 includes a flexible support 32. A first surface (not shown) of the support 32 is adapted to be applied to and conformed to the face of a user. A second surface 36 of support 32 is imprinted with multiple predetermined regions 37, 38. Each imprinted predetermined region 37, 38 on the second surface 36 of support 32 corresponds to an isolated, discrete region (not shown) on the first surface of support 32, each isolated, discrete region corresponding to the location in the mask 30 of a cosmetic composition containing a skin benefit agent. The imprinted predetermined regions 37, 38 aid the user in the placement and use of the mask 30 so as to ensure the most efficacious delivery of the skin benefit agent, i.e. an active material, to the target area of the skin to be treated. The imprinted predetermined regions 37, 38 indicate the location in the mask of corresponding isolated, discrete regions associated with different cosmetic treatment products, in accordance with the unique needs of the user's skin, such as an anti-wrinkle treatment and a tightening or lifting treatment, respectively. The imprinted predetermined regions 38 are shaped and/or sized differently to correspond to different facial contours, e.g. cheek and forehead, and are provided with the same color or graphics to indicate that the corresponding isolated, discrete regions contain the same cosmetic treatment. In a further embodiment of the present invention, the facial mask may be provided with multiple imprinted predetermined regions on the second surface corresponding to multiple isolated, discrete regions on the first surface, at least two of which are associated with the same cosmetic treatment composition, in the same or in different concentrations, for targeted delivery to isolated areas of the facial skin. The cosmetic sheet is provided with openings 42 for the eyes, the nose and the mouth, and preferably also with slits 44, arranged at the peripheral edge of the support 32, to further aid the user in the application and placement of the mask on the face. Once the cosmetic sheet mask is applied to the user's face and manipulated in the manner instructed, the cosmetic treatment composition(s) are released and the appropriate skin benefit agent(s) can provide simultaneous and isolated treatments to different regions of the face, such as forehead, eyes, cheeks, and so forth.

Although the imprinted regions 37, 38 are shown as particular shapes having particular respective patterns thereon, it will be understood by those skilled in the art that the imprinting may be provided as, for example, other solid or unfilled shapes, such as other geometric shapes, or as non-geometric shapes, a pattern, or the like. The imprinting may comprise colors, letters, numbers, words, and so forth, to aid in the correct usage of the product and may correspond to usage instructions provided together with the sheet in a kit form. Printing may be executed using permanent ink, ink that changes color with water or other liquid or gel contact. The printing/design may be mechanically stamped on the sheet, or may be woven into the fabric. As further alternatives, the imprinted predetermined region may be provided as a film, a label, or a patch, or the like, applied to the fabric. The cosmetic composition containing the skin benefit agent or agents may be associated with isolated, discrete regions of the first surface of the support 32 in any manner known to those skilled in the art. Mention may be made, for example, of applying cosmetic compositions containing active ingredients, such as freeze-dried and/or water-activated ingredients, to the second surface 36 of the support 32 in discrete areas so as to overlie the target areas of the skin when the cosmetic sheet 30 is applied to and conformed to moistened skin. Alternatively, the cosmetic compositions may be provided in the form of a film, a label or a patch, which is infused with the skin benefit ingredients, and which is adhered to or capable of being affixed to the first surface of support 32. The amount of the skin benefit agent delivered to the targeted area of the skin may be controlled by methods known in the art, including adjusting the concentration of the skin benefit agent in the composition, the size of the isolated, discrete region and the length of time the cosmetic sheet is in contact with the skin.

Figure 5:
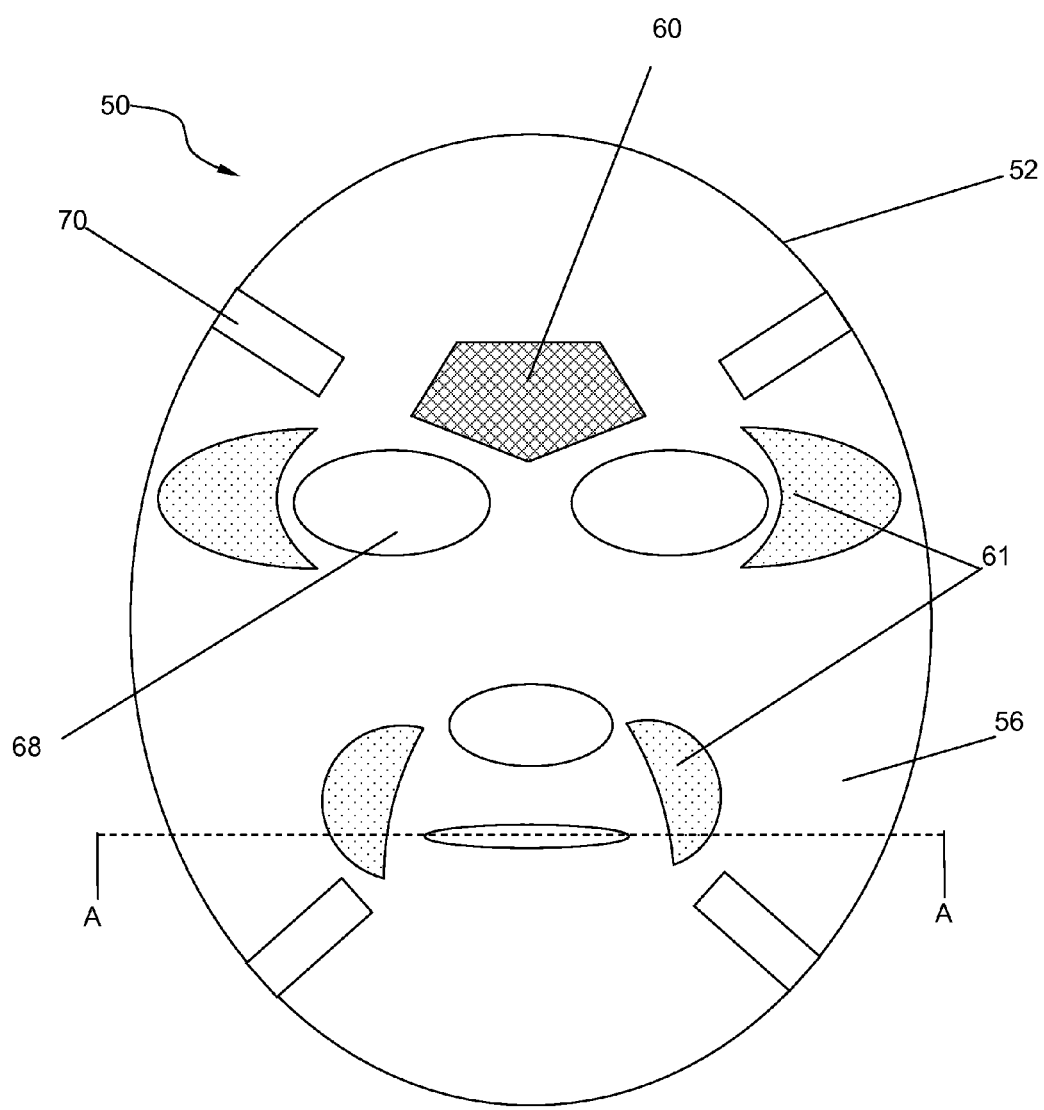
FIG. 5 is a schematic representation of a facial mask according to a fourth embodiment of the present invention.
Figure 6:
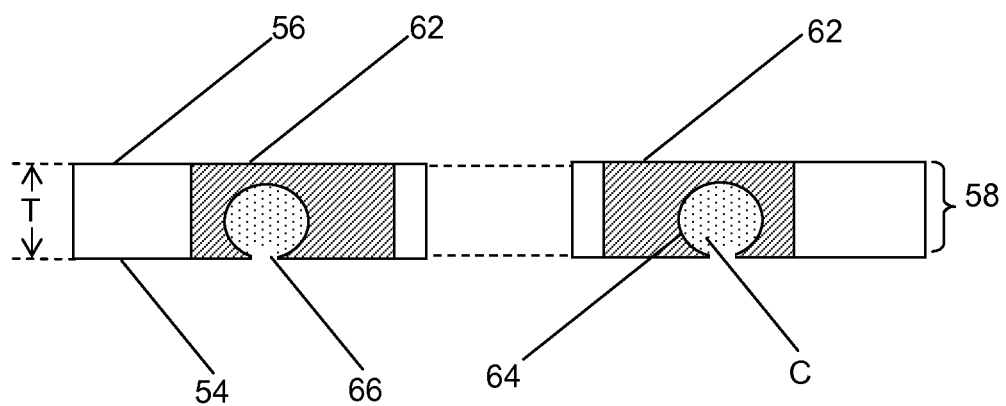
FIG. 6 is a cross-sectional view taken through a portion of the facial mask at A-A shown in FIG. 5.

In FIGS. 5 and 6, a facial mask, designated generally by the numeral 50, is shown. The facial mask 50 has a configuration adapted to conform to facial features. The facial mask 50 includes a flexible support 52 having first and second opposite surfaces 54 and 56, and an interior region 58 in which is located one or more isolated, discrete regions 62 containing one or more skin treatment compositions. In one embodiment of the present invention, the substrate is a monolayer. In another embodiment of the present invention, one or both opposite surfaces 54, 56 may be comprised of a plurality of layers. The first surface 54 of the support 52 is adapted to be applied to and conformed to the face of a user. The second surface 56 of support 52 is imprinted with multiple predetermined regions 60, 61, the imprinted predetermined regions 60, 61 corresponding to the location of isolated, discrete regions in the interior region 58 of the mask 50 containing cosmetic skin treatment compositions, each including at least one skin benefit agent or active. For example, the imprinted predetermined regions 60, 61 may correspond to respective isolated discrete regions containing different treatment compositions, such as an anti-acne composition and a skin soothing composition. In a further embodiment of the present invention, imprinted predetermined regions 60, 61 may correspond to isolated, discrete regions containing the same treatment compositions provided in different concentrations. The imprinted predetermined regions 60, 61 are preferably sized and shaped to contour to the different areas of the face. As shown more particularly in FIG. 6, the interior region 58 of the support 52 contains isolated, discrete regions 62 corresponding to imprinted predetermined regions 61 on the first surface of the mask. Each isolated, discrete region 62 includes at least one reservoir 64 which is at least partly filled with a composition comprising a cosmetic treatment composition C. Each isolated, discrete region 62 contains one or more cosmetic compositions, including one or more skin benefit agents, depending on the specific skin area and skin problems to be targeted.

At least one aperture 66 is associated with each reservoir 64. The at least one aperture 66 is formed in the first surface 54 of support 52 and is in fluid communication with the reservoir 64. Manipulation of the mask material in the imprinted predetermined regions 58 expresses the treatment composition from the reservoirs 64 through apertures 66 in the first surface 58, applying the composition to the target surface of the skin. Apertures 66 may be of any desired size and shape. The use of one or more discrete reservoirs 64 as opposed to a generally porous substance-impregnated material is considered to provide a more controlled dosing functionality for the cosmetic sheets of the present invention. Also contemplated is one reservoir feeding a plurality of apertures. Multiple cosmetic treatment compositions may be employed in the same reservoirs in isolated, discrete regions, or they may be contained in separate discrete regions or in separate reservoirs in a particular discrete region such that the different substances remain segregated prior to use but during use may either remain separate in order to target different areas/needs or may be co-mingled. This may be useful when it is desired to prevent reactions between components prior to use and/or degradation or exhaustion of the active ingredients. The cosmetic substances will be provided in a form which is sufficiently viscous to be retained in the isolated, discrete regions until use, and to avoid extensive migration from the targeted area on the skin once the composition is released. In addition to controlling the viscosity of the cosmetic composition and the concentration of the skin benefit agent in the composition, the reservoir geometry and volume may be designed as desired for ultimate capacity and also rate of delivery of an effective amount of the skin benefit agent to the targeted area of the skin.

The sheet material used in the cosmetic masks according to this embodiment of the present invention has a thickness T which decreases when compressed by a force applied in a direction which is normal to the surface of the sheet. The reservoirs 64 extend inwardly of the first surface 54 into the interior 58 of the sheet, and may be formed, marked, labeled, or otherwise identified by a variety of methods known in the art, such as by stamping, embossing, etc.

The cosmetic sheet is provided with openings 68 for the eyes, the nose and the mouth, and preferably also with slits 70, arranged at the peripheral edge 72 of the support 52, to further aid the user in the application and placement of the mask on the face.

The cosmetic sheets of the present invention may be manufactured in any manner suitable for the intended geometry and intended materials and substances involved. In accordance with the invention, the support will be constructed in a manner so as to deliver the cosmetic composition from the mask in a direction which is toward the target area of the skin. The support may be comprised of a single liquid permeable layer or of a plurality of layers. The material of the first surface of the support may be comprised of a liquid permeable material while the second surface may be comprised of either a liquid permeable or a liquid impermeable layer or may have liquid permeable portions. For example, the second surface may include liquid permeable regions in the printed predetermined areas for the introduction of a liquid or gel activator. The cosmetic sheet according to the present invention may be manufactured by forming the plurality of apertures and reservoirs by thermal embossing with a heated die to the desired depth, and then either injecting the treatment composition into the reservoirs or flooding the treatment composition into the reservoirs and removing the excess composition. The graphics may be applied to the support, as discussed above, or in any other method known in the art for imprinting paper or textiles.

It also is contemplated that a user could customize a cosmetic sheet in accordance with the user's unique skin requirements. The isolated, discrete regions may be provided as pre-filled reservoir-containing pockets, or the like, which could be affixed by the user to different areas of the second surface of the sheet for subsequent release of the active substance to selected areas of the skin. Labels or patches (e.g. geometric shapes, patterns, etc.) could be affixed to the first surface of the sheet to correspond to the designated discrete regions (e.g. reservoir-filled patches) on the second surface of the sheet. A "kit" therefore could be provided with pre-impregnated pockets in different sizes/shapes and with different cosmetic compositions and corresponding patches or labels, and instructions for application for a consumer to use for such customization. The user could then refer to instructions provided in the kit to apply the labels and pre-filled pockets to the sheet to provide appropriate customized treatments to targeted areas of the skin. In that embodiment, the surface of the skin benefit agent-filled pocket which contacts the skin will be comprised of a liquid permeable material so as to deliver the cosmetic composition containing the skin benefit agent from the pocket in a direction which is toward the target area of the skin.

It is further contemplated that a cosmetic sheet could be provided which has imprinted predetermined regions indicated on the second surface, but no discrete areas containing cosmetic product in the mask or associated with the first surface of the sheet, and that a user could introduce a prescribed dose of a cosmetic composition, such as by use of a dropper, to the predetermined areas on the second surface of the sheet for delivery through the sheet to the targeted areas of the skin. Alternatively, the cosmetic sheet could be provided with both imprinted predetermined regions and isolated, discrete regions, associated with cosmetic product, and a consumer could initiate treatment, as instructed by the labeling or so forth in the imprinted predetermined regions on the second surface of the sheet, such as by applying a liquid or gel activator to the labeled areas.

The cosmetic sheet according to the present invention is applied to and conformed to the desired area of cleansed, and optionally, pre-moistened skin. The imprinted regions correspond to the isolated, discrete, cosmetic product-impregnated regions and indicate where the mask will be performing activity. Once applied, the user then manipulates the imprinted areas on the sheet, e.g. facial mask, for example, by pressing or massaging those areas for several seconds, or as otherwise instructed by the imprinting and/or by instructions enclosed in the package, to fully release the specific impregnated formulation to targeted skin areas. It will be appreciated by those skilled in the art that the manipulation of the imprinted areas could heat-activate the skin benefit ingredients, break and release encapsulated ingredients, catalyze a heating or cooling sensation to enhance the performance of the ingredients, and/or increase microcirculation in the skin, or open the pores, and so forth, allowing for deeper penetration of the active agents into the skin. The imprinted regions may also serve to indicate to the user where water or other liquid or gel activator or additional active ingredients could be applied to the cosmetic mask (e.g., using a dropper). After each imprinted area has been manipulated and after the suggested leave-on time, the mask is removed and discarded.

It will be understood by those skilled in the art that, while gel cosmetic sheets suitable for use in the present invention, are naturally tacky, a cosmetic sheet comprised of paper or a textile may require the presence of a cosmetically acceptable adhesive layer associated with the first surface of the support to enhance adherence to the skin. The adhesion of the sheet to the skin may occur via an adhesive compound associated with the surface of the sheet or it may be provided in the form of a gel or liquid, such as water, which moistens the sheet which then clings to skin. The user may also apply the mask to pre-moistened skin. It also is contemplated that the introduction of a liquid activator to the sheet or to specific areas of the sheet could serve to facilitate the adhesion of the sheet to the skin, to activate the impregnated formulation, or both. The cosmetic sheet may also be provided with a supporting sheet which can be removed, e.g. peeled away, before the sheet is applied to the skin. In a preferred but not necessary embodiment of the present invention, the cosmetic sheet may be provided with a protective sheet which retains the cosmetic treatment compositions in association with the sheet (e.g., seals the reservoirs) and which is removed before the cosmetic sheet is applied to the face.

The cosmetic sheet may be formed of any thin, porous, flexible absorbent material, including woven and non-woven fabrics, including felts, paper, natural fibers, synthetic fibers, elastic blends or a mixture thereof. Non-limiting examples include cotton, linen, rayon, thermoplastics, and cellulosics. The sheet material may be a gel, such as a hydrogel, comprised of, for example, agarose or a water-soluble low-substituted cellulose ether which may include methyl cellulose, hydroxyethyl cellulose, hydroxypropyl cellulose, hydroxypropylmethyl cellulose, hydroxypropylhydroxyethyl cellulose, hydroxyethylmethyl cellulose, ethyl cellulose, hydroxyethylethyl cellulose, or carboxymethyl cellulose. Non-woven fabrics are especially preferred from the viewpoints of cost, productivity and aesthetic feel. Examples of preferred non-woven materials include, but are not limited to, natural and synthetic felts, rice paper or cloth, and bamboo cloth.

The sheet material may be a photochromatic material that changes with light or heat activation, for example, due to skin temperature. The color change could be useful as a cue to the consumer that the mask has started to express the cosmetic composition, or an instruction to the consumer, for example, an instruction to manipulate the mask or to remove it. The entire sheet or specific (e.g. imprinted predetermined) regions of the sheet could change color.

In a further preferred but not necessary embodiment of the present invention, both the substrate and the skin benefit agents of the cosmetic sheet are completely water-soluble, so upon application of water or like liquid activator, the cosmetic sheet softens and conforms to the skin, and subsequently, the entire sheet is absorbed by the skin surface without having to be removed.

The size and shape of the cosmetic sheet material will vary with the target area to be treated. For example, cosmetic sheet material shaped to fit the face may have a surface area ranging from about 0.25 cm$^2$ to about 500 cm$^2$, preferably from about 1 cm$^2$ to about 400 cm$^2$. The sheet will typically have an average thickness of from about 0.5 mm to about 20 mm, preferably from about 0.7 mm to about 5 mm.

As described herein, a kit comprising cosmetic sheet material, and one or more of labels, pre-filled pockets, instructions, e.g. written instructions, a leaflet, a pamphlet, software, etc., which correlate to the graphics imprinted on the cosmetic sheet, is also provided in accordance with the present invention. One or more cosmetic sheets may be provided in a sealed, moisture proof package such as a foil & plastic coated packette. The packettes may contain a plastic tray which holds each sheet flat so as to keep it from folding or rolling over. A number of said packettes may be included in each kit possibly packaged in a folding carton/box. The kit may also contain any skin benefit containing cosmetic compositions, and/or required activator liquid or gel and a dropper for application to the cosmetic sheet material. An applicator tool such as a "wand" or spatula may be included to aid in massage or application/manipulation of the sheet.

Although the present invention has been described in accordance with preferred embodiments, it will be understood by those skilled in the art that various changes and modifications may be made without departing from the spirit and scope of the invention.

What is claimed is:

1. A cosmetic facial mask for targeted and simultaneous treatment of multiple skin conditions associated with facial skin of a user, wherein the facial skin of the user comprises at least two isolated, discrete regions, each isolated, discrete region being associated with a different skin condition, the cosmetic facial mask comprising:
   a flexible substrate being shaped to fit facial features of the user and having openings for eyes, nose and mouth, and the substrate being constructed of a water-soluble gel and including at least two isolated, discrete regions, each of the at least two discrete regions being imprinted with a different skin benefit agent for releasable delivery to a respective one of the at least two isolated, discrete regions of the facial skin associated with said different skin conditions, in amounts effective to simultaneously treat the different skin conditions when the substrate is applied to the facial features of the user, and wherein both the substrate and the skin benefit agents are adapted to can be completely absorbed by the skin of the user after application of the facial mask thereon.

2. The cosmetic facial mask of claim 1, wherein the isolated, discrete regions of the substrate are imprinted with skin benefit agents selected the group consisting of: (1) anti-wrinkle or skin-tightening agents; (2) anti-aging agents; (3) moisturizing agents; (4) skin whitening or depigmentation agents; (5) anti-inflammatory agents; (6) anti-acne agents; (7) skin lipid barrier repair agents; (8) anti-cellulite agents; (9) wound-healing agents; (10) stretch-mark/scar removing agents; (11) plumping agents; (12) hair growth retardation agents; (13) hair growth stimulating agents; (14) dark cycle reduction or de-puffing agents; (15) collagen synthesis or blood circulation enhancing agents; (16) antioxidants; (17) sebum-controlling agents; and (18) pore-minimizing agents.

3. The cosmetic facial mask of claim 1, wherein at least one of the isolated, discrete regions of the substrate contains two or more different skin benefit agents, and wherein the different skin benefit agents are imprinted onto the substrate as separate droplets without being mixed with one another.

4. The cosmetic facial mask of claim 1 wherein at least two of the isolated, discrete regions of the substrate are imprinted with different skin benefit agents for releasable delivery to at least two of the user's T-zone, corner of eye, under eye, corner of mouth, forehead, nose, cheek and jaw line.

* * * * *